US00PP33969P2

(12) United States Plant Patent
Bloom

(10) Patent No.: US PP33,969 P2
(45) Date of Patent: Feb. 22, 2022

(54) ***AJUGA* PLANT NAMED 'ABFG0413A'**

(50) Latin Name: *Ajuga reptans*
Varietal Denomination: ABFG0413A

(71) Applicant: Adrian Bloom, Bressingham (GB)

(72) Inventor: Adrian Bloom, Bressingham (GB)

(73) Assignee: Blooms Nurseries Limited

( * ) Notice: Subject to any disclaimer, the term of this patent is extended or adjusted under 35 U.S.C. 154(b) by 0 days.

(21) Appl. No.: 17/401,171

(22) Filed: Aug. 12, 2021

(51) Int. Cl.
*A01H 6/00* (2018.01)
*A01H 5/02* (2018.01)

(52) U.S. Cl.
USPC ..... Plt./401

(58) Field of Classification Search
USPC ..... Plt./401
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Ajuga reptans* plant named 'ABFG0413A' is disclosed, characterized the unique combination of bronze/purple foliage with a purple flower. The new variety is a *Ajuga*, plants are useful for a variety of ornamental purposes, including outdoor containers and landscape.

2 Drawing Sheets

Latin name of the genus and species: *Ajuga reptans.*
Variety Denomination: 'ABFG0413A'.

BACKGROUND OF THE INVENTION

The new *Ajuga* cultivar is the product of chance discovery. The new variety was discovered as a spontaneous seedling of unknown parentage. The discovery was made in at the inventor's home garden.

The discovery was made in the inventor's garden in Bressingham, England, during March of 2014.

Asexual reproduction of the new cultivar 'ABFG0413A' was first performed in Bressingham, England, by terminal vegetative cuttings in Spring of 2014. 'ABFG0413A' has since produced multiple generations and has shown that the unique features of this cultivar are stable and reproduced true to type.

SUMMARY OF THE INVENTION

The cultivar 'ABFG0413' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABFG0413A' These characteristics in combination distinguish 'ABFG0413A' as a new and distinct *Ajuga reptans* cultivar:

1. Purple flower color in combination with a bronze-purple leaf.

PARENTAL COMPARISON

The parentage is unknown.

COMMERCIAL COMPARISON

Plants of the new cultivar 'ABFG0413A' are comparable to the well-known commercial variety, *Ajuga* 'Mahogany', unpatented. Plants are similar in most horticultural characteristics; however, the new variety 'ABFG0413A' differs in the following:

1. Flowers of the new variety are purple; flowers of this comparator are blue.
2. Foliage of the new variety is narrower than foliage of this comparator.

BRIEF DESCRIPTION OF THE PHOTOGRAPHS

Figure 1:
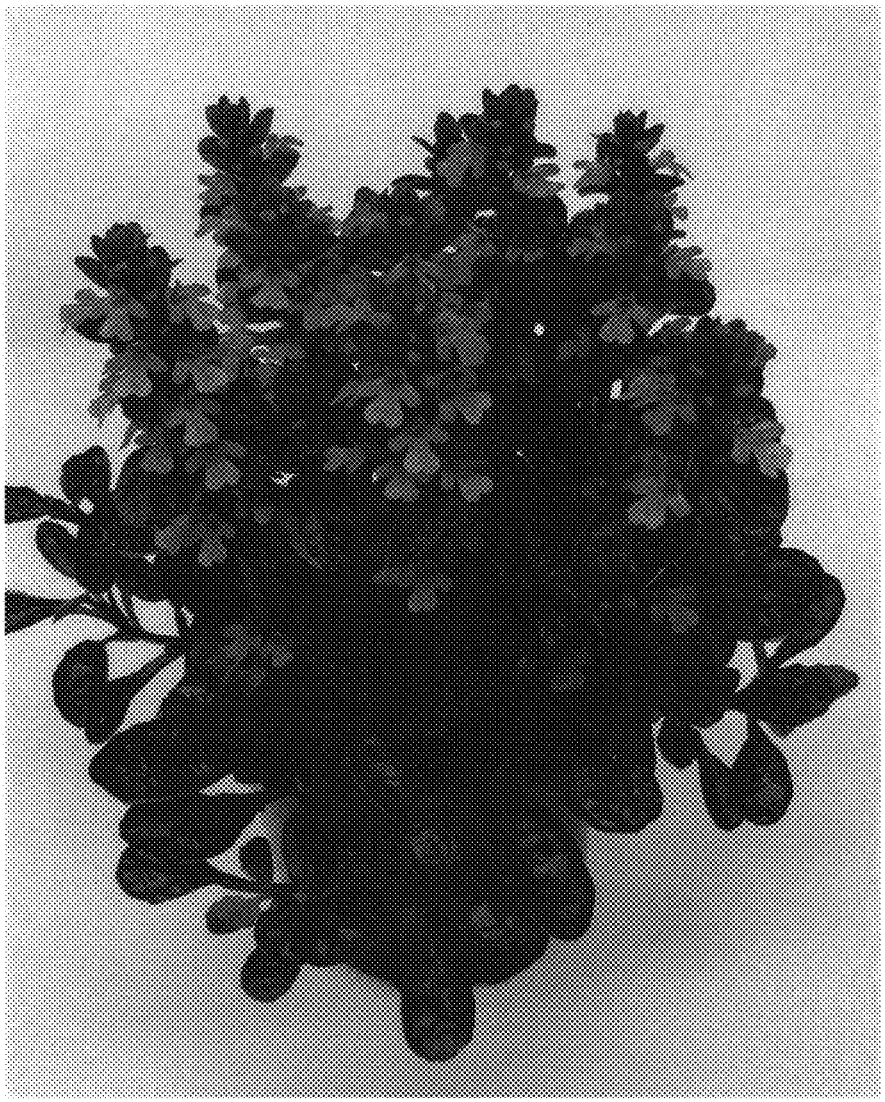

The accompanying photograph in FIG. 1 illustrates in full color a typical plant of 'ABFG0413A' grown outdoors in Bressingham, England. Age of the plant is approximately 8 months.

Figure 2:
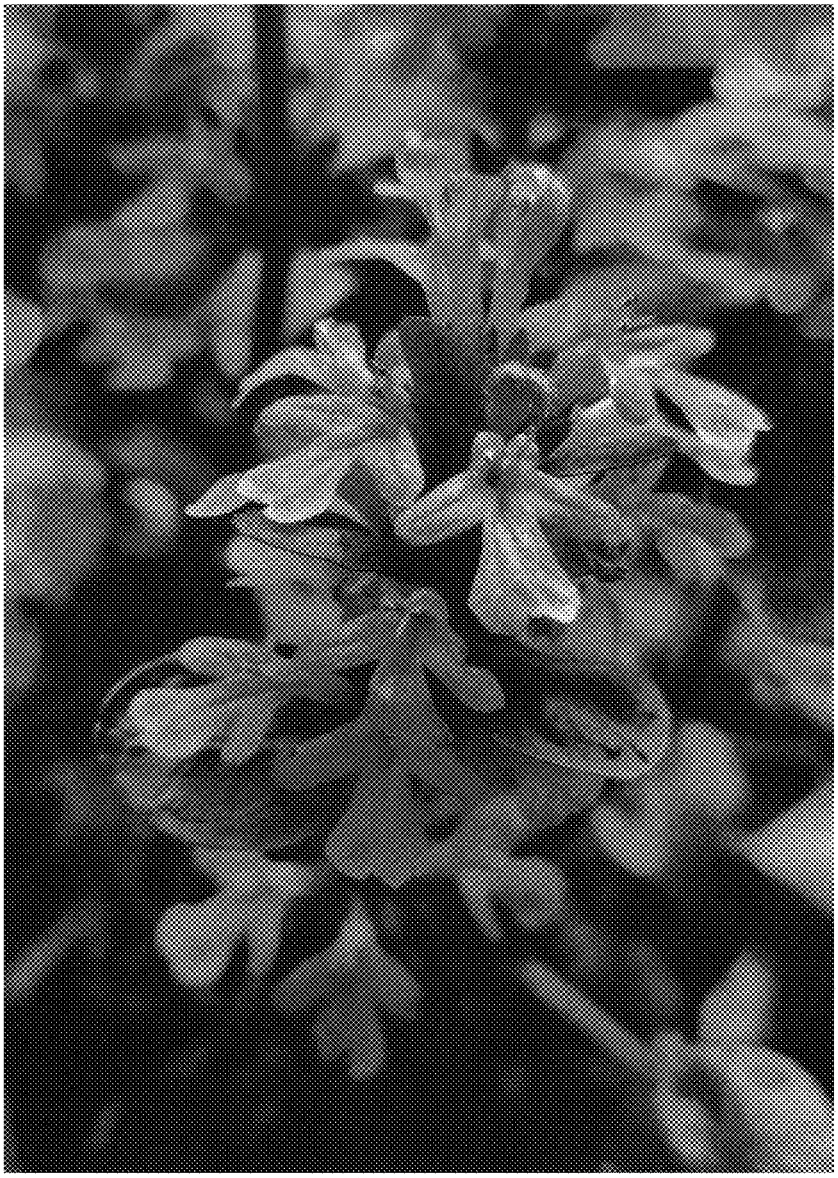

FIG. 2 illustrates a closer view of the foliage and flowers.

The photographs were taken using conventional techniques and although colors may appear different from actual colors due to light reflectance it is as accurate as possible by conventional photographic techniques. No artificial light, photoperiodic treatments or chemical treatments were given to the plants.

DETAILED BOTANICAL DESCRIPTION

In the following description, color references are made to The Royal Horticultural Society Colour Chart, 2015 except where general terms of ordinary dictionary significance are used. The following observations and measurements describe 'ABFG0413A' plants grown outdoors in East Sussex, United Kingdom. Temperatures ranged from approximately 0° C. to 15° C. during the day and approximately −5° C. to 10° C. at night. Measurements were taken during May of 2021. No artificial light, photoperiodic treatments or chemical treatments given to the plants. Measurements and numerical values represent averages of typical plant types. Botanical classification: *Ajuga reptans* 'ABFG0413A'.

PROPAGATION

Type of propagation typically used: Terminal vegetative cuttings. Plant may also be propagated by tissue culture.

Time to initiate roots: About 20 to 30 days at approximately 15° C.

Root description: Fine and fibrous, creamy white, not accurately measured with a color chart.

Aerial root description: Creamy white, 0.1 cm diameter not accurately measured with a color chart.

PLANT

Age of plant described: Approximately 5 months.

Container size of the plant described: 15 cm.

Growth habit: Herbaceous perennial, trailing habit.

Height: Approximately 3 cm.

Plant spread: 32 cm.

Growth rate: Moderate.

Length of primary stem: 8 cm.

Characteristics of main stem:

*Form*.—Tetragonal.

*Diameter*.—About 0.2 cm.

*Color*.—RHS Yellow-Green 146B flushed with Greyed-Purple 183B.

*Texture*.—Glabrous.

*Strength*.—Moderate to strong.

Branching characteristics: Free branching, basal and lateral branches. Pinching is not required, but increases branching.

Length of primary lateral branches: Average 21.6 cm.

Diameter of lateral branches: 3.5 mm.

Quantity of primary lateral branches: 10 to 12.

Length of primary lateral branches: 13 cm.

Characteristics of primary lateral branches:

*Form*.—Stoloniferous.

*Diameter*.—0.2 cm.

*Color*.—RHS Yellow-Green 146B flushed with Greyed-Purple 183B.

*Texture*.—Glabrous.

*Strength*.—Moderate to strong.

Internode length: 2.9 cm.

FOLIAGE

Leaf:

*Type*.—Simple.

*Arrangement*.—Opposite.

*Average length*.—Approximately 15 cm.

*Average width*.—Approximately 3.3 cm.

*Shape of blade*.—Oblong-obovate; juvenile leaves obovate.

*Apex*.—Obtuse.

*Base*.—Attenuate.

*Attachment*.—Sessile.

*Margin*.—Entire, slightly undulate.

*Texture of top surface*.—Rugose, punctate and sparsely puberulous.

*Texture of bottom surface*.—Glabrous, foveolate.

*Appearance of top surface*.—Slightly glossy.

*Appearance of bottom surface*.—Matte.

*Leaf internode length*.—Approximately 3 cm.

*Color*.—Young foliage upper side: RHS Yellow-Green 147A, heavily flushed with Greyed-Purple 187C. Young foliage under side: RHS Yellow-Green 146B. Mature foliage upper side: RHS Yellow-Green 146B heavily flushed with Greyed-Purple N186C. Mature foliage under side: RHS Yellow-Green 147B.

*Venation*.—Type: Pinnate. Venation color upper side: RHS Greyed-Purple 187B and N186C. Venation color under side: RHS Yellow-Green 147B and 148A.

*Petiole*.—Not present.

FLOWER

Natural flowering season: Spring: March to May in England in a typical year.

Inflorescence (raceme): Verticillaster.

*Height*.—12 cm.

*Diameter*.—3.4 cm.

*Quantity of flowers per* (*average range*).—Inflorescence has 7 to 9 whorls of flowers; each whorl has 6 or 7 flowers.

Peduncle:

*Length*.—4.0 to 4.5 cm.

*Diameter*.—2.5 cm.

*Texture*.—Smooth, sparsely puberulous.

*Color*.—Near RHS Yellow-Green 146B flushed with Greyed-Purple 183B.

*Orientation*.—Near vertical.

*Strength*.—Medium to strong.

Individual flowers:

Flower longevity on plant: 4 to 6 days.

Bud:

*Shape*.—Globular.

*Length*.—0.4 cm.

*Diameter*.—0.25 cm.

*Color*.—RHS Purple N78D.

*Petal arrangement*.—The corolla is sympetalous and typically bilabiate with 2 small, highly fused lobes forming an upper lip and 3 larger highly fused lobes forming a lower lip.

Size:

*Diameter*.—Approximately 0.9 cm. at widest point.

*Length*.—Approximately 1.1 cm.

*Persistence*.—Persistent.

*Fragrance*.—None observed.

Petals:

*Margin*.—Entire.

*Tip shape*.—Upper lip: attenuate. Lower lip: emarginate.

*Length*.—Upper lip: 0.25 cm. Lower lip: 0.7 cm. Tube: 0.7 cm.

*Width*.—Upper lip: 0.25 cm. Lower lip: 1.2 cm. Tube: 0.15 to 0.2 cm.

*Texture*.—Upper lip: glabrous. Lower lip: glabrous, sparsely lanate on outer surface. Tube: glabrous.

Color:

*Upper lip*.—When opening: Inner surface: Near RHS Purple 77B. Outer surface: Near RHS Purple 77B. Fully opened: Inner surface: Near RHS Purple 77B. Outer surface: Near RHS Purple 77B. Fading: Inner surface: Near RHS Purple 77B. Outer surface: Near RHS Purple 77B and 77C.

Color:

*Lower lip*.—When opening: Inner surface: Near RHS Purple N78B. Outer surface: Near RHS Purple 77C. Fully opened: Inner surface: Near RHS Purple N78B to N78C. Outer surface: Near RHS Purple 77C. Fading: Inner surface: Near RHS Purple N78B to N78C. Outer surface: Near RHS Purple 77C.

Color:

*Tube*.—When opening: Inner surface: Near RHS Purple 77C. Outer surface: Near RHS Purple N78C. Fully opened: Inner surface: Near RHS Purple 77C. Outer surface: Near RHS Purple N78C. Fading: Inner surface: Near RHS Purple 77C. Outer surface: Near RHS Purple N78C.

Sepals:

*Shape*.—Quantity per flower: 5 — basally fused.
*Length*.—Approximately 0.3 cm.
*Width*.—Approximately 0.1 cm.
*Margin*.—Entire.
*Texture*.—Puberulous.
*Color*.—Near RHS Purple N77A.

Pedicels:

*Length*.—0.05 to 0.1 cm.
*Diameter*.—0.05 cm.
*Angle*.—About 75° to the lateral branch.
*Strength*.—Moderate.
*Texture*.—Glabrous.
*Color*.—RHS Purple N77A.

REPRODUCTIVE ORGANS

Stamens:

*Number*.—4. Filament: 0.8 cm long, white/translucent.

Anthers:

*Shape*.—Reniform.
*Length*.—Less than 0.1 cm.
*Color*.—RHS Yellow-Green 152B.
*Pollen*.—Color: RHS Blue 103B. Quantity: Very sparse.

Pistil:

*Number*.—1.
*Length*.—0.8 cm.
*Style*.—Length: less than 0.1 cm. Color: White, not accurately measured with R.H.S. chart.
*Stigma*.—Shape: Filiform. Color: RHS Purple 77C. Ovary Color: RHS Green 143C.

OTHER CHARACTERISTICS

Fruits and seeds: Not observed to date.
Temperature tolerance: Observed cold hard to −10° C.
Disease/pest resistance: Neither resistance nor susceptibility to normal diseases and pests of *Ajuga* observed.
Drought tolerance: No drought resistance observed.

What is claimed is:

1. A new and distinct cultivar of *Ajuga* plant named 'ABFG0413A' as herein illustrated and described.

* * * * *